*(12)* United States Patent
Chaumonnot et al.

(10) Patent No.: US 9,512,050 B2
(45) Date of Patent: Dec. 6, 2016

(54) PROCESS FOR DEHYDRATION AND ISOMERIZATION OF ALCOHOLS USING A CATALYST BASED ON A MESOSTRUCTURED MATERIAL COMPRISING SILICON

(71) Applicant: IFP ENERGIES NOUVELLES, Rueil-Malmaison (FR)

(72) Inventors: Alexandra Chaumonnot, Lyons (FR); Vincent Coupard, Villeurbanne (FR); Sylvie Maury, Saint Maurice d'Argoire (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 427 days.

(21) Appl. No.: 13/853,410

(22) Filed: Mar. 29, 2013

(65) Prior Publication Data

US 2014/0296596 A1    Oct. 2, 2014

(30) Foreign Application Priority Data

Mar. 29, 2012   (FR) ...................... 1200950

(51) Int. Cl.
| | | |
|---|---|---|
| *C07C 1/24* | (2006.01) | |
| *C07C 5/25* | (2006.01) | |
| *B01J 29/03* | (2006.01) | |
| *B01J 29/04* | (2006.01) | |
| *B01J 35/10* | (2006.01) | |
| *B01J 37/00* | (2006.01) | |
| *C07C 5/27* | (2006.01) | |

(52) U.S. Cl.
CPC .......... *C07C 5/2518* (2013.01); *B01J 29/0308* (2013.01); *B01J 29/041* (2013.01); *B01J 35/1061* (2013.01); *B01J 37/0045* (2013.01); *C07C 1/24* (2013.01); *C07C 5/2775* (2013.01); *C07C 2521/12* (2013.01); *C07C 2529/70* (2013.01); *C07C 2529/80* (2013.01); *C07C 2529/86* (2013.01); *C07C 2529/87* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,503,818 A | * | 4/1996 | Nicolaides ................... 585/671 |
| 7,589,041 B2 | * | 9/2009 | Ying et al. ..................... 502/64 |
| 2013/0245348 A1 | * | 9/2013 | Vermeiren et al. ........... 585/324 |

FOREIGN PATENT DOCUMENTS

| | | |
|---|---|---|
| WO | WO-2006 031259 | 3/2006 |
| WO | WO-2006 070073 | 7/2006 |
| WO | WO-2011 154621 | 12/2011 |

OTHER PUBLICATIONS

Zhang et al. Applied Catalysis A: General 403 (2011) 1-11.*
IFP Energies Nouvelles, "Process for dehydration and isomerization of C4 alcohols using an amorphous solid with suitable porosity," Espacenet, Publication Date: Dec. 15, 2011; English Abstract of WO-2011 154621.
Search Report for FR1200950, Date of the actual completion of search: Dec. 6, 2012.
Van De Water, L. G. A. et al., "Improved catalytic activity upon Ge incorporation into ZSM-5 zeolites," Journal of Catalysis, Apr. 2004, vol. 223, No. 1, pp. 170-178.
Zhang, C. et al., "Synthesis and characterization of composite molecular sieves with mesoporous and microporous structure from ZSM-5 zeolites by heat treatment," Microporous and Mesoporous Materials, Aug. 28. 2003. vol. 62. No. 3. pp. 157-163.

* cited by examiner

*Primary Examiner* — In Suk Bullock
*Assistant Examiner* — Sharon Pregler
(74) *Attorney, Agent, or Firm* — Millen White Zelano and Branigan, PC; John Sopp; Anthony Zelano

(57) ABSTRACT

This invention has as its object a process for simultaneous dehydration and skeletal isomerization of a feedstock that comprises at least one $C_4$ monoalcohol and that contains between 0.5 and 50% water, for the purpose of producing $C_4$ alkenes, with said process operating at a temperature of between 250 and 550° C., under a pressure of between 0.1 and 1 MPa, with an hourly volumetric flow rate of between 0.1 and 10 h-1, characterized in that it uses a catalyst that comprises at least one mesostructured material that comprises silicon and at least one element X that is selected from among aluminum, boron, gallium, indium, and germanium.

9 Claims, No Drawings

PROCESS FOR DEHYDRATION AND ISOMERIZATION OF ALCOHOLS USING A CATALYST BASED ON A MESOSTRUCTURED MATERIAL COMPRISING SILICON

TECHNICAL FIELD OF THE INVENTION

This invention relates to an improved process for the production of $C_4$ alkenes or butenes from feedstock of $C_4$ monoalcohols or butanols. The butanol feedstock that is used is of biological or chemical origin. This process uses a catalyst that comprises at least one mesostructured material that comprises silicon.

The alkenes that are obtained, in particular isobutene and butene-1, have an important advantage in the field of petrochemical industry and organic synthesis, with the isobutene being a key compound in the chemistry of major intermediate compounds.

PRIOR ART

The study of the state of the art showed that the majority of works dealt either with the dehydration reaction of alcohols (optionally with a simultaneous appearance of a secondary reaction for positional isomerization of alkenes that are formed) or with the reaction for isomerization of an olefinic feedstock that involves in particular a positional isomerization and a skeletal isomerization. A brief summary of the primary results dealing with these two separate reactions is presented below. Furthermore, several works focus on the simultaneous implementation of these two reactions and are described in the last portion of this paragraph.

The dehydration reaction of the alcohols leads to the formation of alkenes. Based on the type of process implemented, operating conditions applied and the nature of the catalyst that is used, secondary reactions can occur, the most common being the formation of ethers from the initial feedstock or else the formation of positional isomer alkenes from alkenes originally formed during dehydration. The nature of the acid sites considered as active ingredients for this reaction has been discussed extensively in literature. Some state that only the Bronsted sites are active, others that the Lewis acid/Bronsted base pairs are responsible for the dehydration for forming the corresponding alkene.

The aluminum solids are known for having acid/base pairs and are encountered extensively in literature as dehydration catalysts. For example, the article by Adkins et al., J. Am. Chem. Soc. 1925, 47, 1163 will be cited, where it is noted that alumina, after activation in air, is effective for a short period for dehydration of numerous alcohols. It seems, however, that the aluminum solids have a tendency also to promote the secondary reaction of the formation of ethers, owing to the nature of presumably involved active sites.

Numerous other solids have been studied for the dehydration reaction of $C_4$ alcohols (primarily for the synthesis or the purification of isobutene), with, in particular, the use of zeolitic solids or else aluminosilicic solids. In related works, the hypothesis of Bronsted-acid-type active sites is generally adopted. For example, the works of P. Berteau et al., described in Applied Catalysis, 1991, 70, 307, which studied the acido-basic properties of silica-aluminas with variable contents of Si and Al, will be cited. These variable acido-basic properties were correlated with the catalytic properties in the dehydration reaction of 1-butanol. The authors conclude that only the alumina-rich solids (low Bronsted acidity), only the dehydration of 1-butanol into butene-1, as well as the formation of ether (dibutyl ether) take place. In contrast, only the silica-rich solids (more pronounced Bronsted acidity), the dehydration into butene-1, and the rapid positional isomerization into butene-2 cis and trans take place. We note that no reaction of skeletal isomerization has been observed. The article by Makarova et al., J. Catal., 1994, 149, 36 will also be cited, where it is taught that the MFI (ZSM-5) zeolite and the amorphous silica-aluminas are active in dehydration of 1-butanol. The positional isomerization of formed butenes is also mentioned, as well as the formation of ethers (dibutyl ethers). However, again, no skeletal isomerization is demonstrated. Let us emphasize that these authors have demonstrated an effect of the size of the ZSM-5 zeolite crystals on the selectivity of isomerization of butene-1 into butene-2. Thus, a significant impact of the containment impact can be observed, the crystals of larger size bringing about a more significant isomerizing activity. It should be noted also that a strong deactivation is observed on these zeolites at a test temperature of 165° C., probably linked to the formation of coke.

In a general way, we note that the dehydration reaction of monoalcohols on weakly acidic solids such as the aluminas or amorphous silica-aluminas is carried out at relatively low temperatures (300° C. or less).

The skeletal isomerization of butenes requires stronger Bronsted sites and higher reaction temperatures than the dehydration. The alumina, which has weak acid sites, is therefore used in industrial processes at very high temperatures (>470° C.) and in the presence of water so as to limit the polymerization reactions. This is the case in particular of the IFPEN/Axens ISO-4 process described in the U.S. Pat. No. 5,545,793. More specifically, this patent relates to a process for isomerization of the skeleton and the position of the double bond of $C_4$ olefins using an alumina-based material, having undergone a particular shaping in the presence of a polyorganosiloxane. This reaction is used in a process where the water is co-introduced with the olefinic feedstock so as to limit the parasitic reactions as mentioned above. The alumina-based catalysts are advantageous to the extent that they are robust and less costly and operate in regenerative mode. Nevertheless, the tests provided in the example indicate performance levels obtained at temperatures of higher than 400° C. after 1 hour of operation, which is relatively short and can only allow one to think that the stability of the catalyst over time remains perfectible. With the skeletal isomerization reaction always being accompanied by undesirable secondary reactions, a loss of activity of the catalyst can be explained by coking reactions.

The zeolites, known for their strong Bronsted acidity, are frequently used. Thus, the zeolites with a mean size of channels (10 MR) have been extensively studied for this application. The activities of ZSM-23, ferrierite and ZSM-5 in acid form have been compared for the isomerization of 1-butene into isobutene by Young et al., J. Catal. 1995, 151, 467. The ferrierite zeolite is by far the most active even if it has a high deactivation speed. Young et al. compared ZSM-23, ferrierite and ZSM-5 of Si/Al 8.8, 65 and 87 at temperatures of 420 (FER and MTT) and 500° C. (MFI) and pph of 8 (FER and MTT) and 100 (MFI, to limit the secondary reactions). In the case of ZSM-5, the size of intersections between channels would promote the formation of oligomerization products and the parasitic reactions of cyclization, aromatization by transfer of hydrogen and cracking. Even at very high vvh (hourly volumetric flow rate), the isobutene yield is mediocre. It is possible that the special feature of this zeolite of having zig-zag channels increases the dwell time of the butenes and therefore the secondary reactions such as oligomerization and cracking. In contrast, the ferrierite would promote the diffusion of the butenes owing to its two-dimensionality and its straight channels limiting the secondary reactions. In addition, its small channel size would also prevent the formation of butene dimer. The ZSM-23 is more stable than the ferrierite but promotes the secondary reactions.

For this reaction, as for the dehydration reaction, we note that the structural type of the zeolite, i.e., the size and the morphology of channels defined by the crystalline network, is essential for orienting the activities and the selectivities of the reactions.

We saw above that the two "dehydration" and "isomerization" reactions, when they are independent, require different acidities and temperatures (among other parameters). In addition, Kotsarenko et al. (Kinetika i Kataliz, Vol. 24, No. 4, pp. 877-882, July-August, 1983) demonstrated that the skeletal isomerization kinetics of isobutene of the one-pot product derived from isobutanol was much faster than the isomerization kinetics of an isobutene feedstock. Thus, a catalyst that is active in non-isomerizing dehydration at low temperature or in skeletal isomerization at higher temperature will not necessarily be high-performing in one-stage dehydration/isomerization. In addition, the oxidized elements that are present in low content in an olefinic fraction are known inhibitors of the skeletal isomerization reaction of olefins. The simultaneous implementation of these two reactions therefore is not trivial. However, several works have taken the approach of more specifically studying both the dehydration and isomerization reactions for the purpose of ultimately promoting skeletal isomerization. Thus, the works described in Applied Catalysis A: General, 2001, 214, 251 relate to simultaneous dehydration and isomerization (skeletal or positional) of the double bond, on $C_4$ alcohols. In these works, gamma-aluminas that are optionally activated with sulfuric acid have been used at very low GHSV (Gas Hourly Space Velocity: mass flow rate of feedstock per volume of catalyst per hour) with different monoalcohols comprising an aliphatic chain with 4 carbons to evaluate their selectivity in terms of production of corresponding olefins and in other undesired products such as methane, ethane, ethylene, propane, propylene, and the $C_5^+$ products. It is thus demonstrated that an alumina that is activated with sulfuric acid is more active and more selective than an alumina of commercial origin for the combined application targeted, namely the dehydration combined with the isomerization of the skeleton and the position of the double bond of the resulting olefins. According to this document, it therefore seems that the most acidic alumina possible is necessary for jointly implementing the dehydration and isomerization of $C_4$ monoalcohols. The selectivities of linear butenes from isobutanol (skeletal isomerization) are not, however, improved by the activation of alumina with sulfuric acid. In addition, no mention is made of the stability of the performance levels of this solid over time under load. It should be noted that, in a publication by the same team, Applied Catalysis A, 2000, 203, 5, the skeletal-isomerization activity of n-butenes of alumina activated with sulfuric acid that is prepared according to the same operating procedure lasted only 5 to 6 hours, with these solids requiring regeneration in air every 6 hours. Several studies have also dealt with the potential of commercial zeolites in the dehydration and isomerization reactions of n-butanol. Chadwick et al. in particular described in Applied Catalysis A, 2001, 403, 1 the one-stage dehydration and isomerization of n-butanol for forming isobutene on unmodified commercial acid zeolites. It compares in particular the performance levels of zeolite of a mean size of channels (10 MR) such as theta-1, ZSM-23, ferrierite, ZSM-5, SAPO-11 and Y, with the more stable zeolites being the monodimensional ones (theta-1 and ZSM-23), ferrierite being deactivated by coking and SAPO-11 being dealuminified under the action of water produced by the dehydration reaction. We also note that in this study using zeolites, high GHSV have to be used (5,200 $h^{-1}$) to limit the secondary reactions, and that, despite these conditions, the reactions of oligomerization, cracking and hydrogen transfer bring about a significant loss in butene yield.

In contrast, to the extent that the reaction for isomerization of butenes formed by dehydration of $C_4$ alcohols is a reaction consecutive to the latter, it is obvious that the contact time (and on the scale of the active site, the monitoring of the diffusion in the pores) has to be optimal for promoting this reaction starting from primary products of the reaction. In contrast, it is to be weak enough to limit the oligomerization reactions of the formed products. This influence of the contact time between the reagent and the catalyst has been studied extensively, and the works already mentioned above will be cited (Applied Catalysis A: General, 2001, 214, pp. 251-257). Thus, it was demonstrated that a shorter contact time (high GHSV) limited the secondary oligomerization reactions.

We note that the great majority of publications and patents above relate to the production of isobutene from linear butanols. This is explained, on the one hand, by the fact that isobutene is a key molecule of petrochemistry, just as for the synthesis of gasoline additive such as ETBE and MTBE, and, on the other hand, because the linear butanols are more easily produced by conventional fermenting methods (ABE) than isobutanol. Nevertheless, recent developments have made it possible to greatly improve the isobutanol yields, making this feedstock accessible and available at an attractive cost. As we noted in this state of the art, the dehydration of $C_4$ alcohols on acid solids is generally accompanied by the positional isomerization of the formed alkene. These two reactions are actually concomitant, since the positional isomerization of the double bond of the alkene is as fast as the dehydration reaction of the $C_4$ monoalcohol.

In the case of isobutanol, the isobutene that is initially formed becomes protonated easily (favorable formation of a tertiary carbocation) and can then undergo secondary reactions, in particular of dimerization and then of cyclization. This runs the risk of bringing about the formation of undesired secondary products.

The patent application WO 2011/113834 A1 describes a process for simultaneous dehydration and skeletal isomerization of isobutanol for the purpose of producing corresponding olefins on crystalline silicate catalysts, which may or may not be dealuminified, may or may not be modified with phosphorus, the group FER, MWW, EUO, MFS, ZSM-48, MTT, MFI, MEL or TON having an Si/Al ratio that is greater than 10, silicoaluminophosphate molecular sieves of the group AEL, or silica-alumina, zirconia-alumina, titanium-alumina, or fluorine-alumina. In the examples, the authors demonstrate very good selectivity of isomers of the isobutene with a high WHSV (feedstock mass per catalyst mass per hour) on H-FER zeolite and on phosphorus-modified HZSM-5, with the modified ZSM-5 bringing about the formation of a maximum 10% of heavy compounds ($C_5^+$). No concept of stability of these performances is mentioned in this document. The only other catalyst shown is gamma-alumina.

The document WO 2011/154621 describes a process for the production of $C_4$ olefins starting from a $C_4$ monoalcohol feedstock by dehydration and skeletal isomerization in the same reaction chamber, with these reactions being implemented in the presence of an alumina-based catalyst, free of halogens and having a pore distribution such that the volume of pores with a diameter that is greater than 0.1 µm, i.e., in the field of macropores, is between 10 mL/100 g and 30 mL/100 g. This document teaches that the pore distribution that is rich in emergent macroporosity is advantageous and is therefore oriented toward the use of solids that are rich in macroporosity.

The document WO 2006/031259 describes the totally crystallized mesoporous zeolitic materials. These materials can be used, according to this document, for the implementation of a multitude of reactions, among which are the reactions of isomerization, halogenation of aromatic compounds, oxidoreduction, dehydration, condensation, hydroformylation, etc. As indicated above, it is known that the zeolites can be used to catalyze a multitude of reactions. This document, which focuses on the methods for synthesis of mesostructured zeolitic materials, is mute on the useful characteristics in the simultaneous catalysis of the dehydration and skeletal isomerization reactions.

The state of the art above therefore makes mention of different families of oxides, such as the family of zeolites, aluminas, silicated aluminas, etc., as potential catalysts for the production of $C_4$ alkenes starting from a $C_4$ monoalcohol feedstock as described in this invention. To our knowledge, no works of open literature and no patent make mention of the use of mesostructured solids and in particular mesostructured aluminosilicate solids as constituent elements of catalysts or directly as catalysts of reactions of the process of this invention. The mesostructured aluminosilicate solids constitute a specific family of oxide solids of the mesoporous aluminosilicate type that have particular textural, structural and acidity properties. Only some patents make mention of the use of these solids as potential catalysts of dehydration or as potential catalysts for isomerization of hydrocarbon feedstocks (FR 2,872,151, FR 2,886,637). Likewise, a single publication, Catalysis Letters, 2007, 119 describes the use of Al-MCM-41 mesostructured solids in the positional isomerization reaction of 2-butene for forming 1-butene, but has not observed skeletal isomerization of the double bond. No formation of isobutene is therefore observed contrary to the case of the use of the ferrierite zeolite, studied in these works by way of comparison. The applicant discovered that it was possible to use this type of solid to simultaneously implement the dehydration of a $C_4$ monoalcohol and the skeletal isomerization of the $C_4$ alkene thus formed, with all of the "process" constraints linked to this combination.

OBJECT AND ADVANTAGE OF THE INVENTION

This invention has as its object a process for simultaneous dehydration and skeletal isomerization of a feedstock that comprises at least one $C_4$ monoalcohol and that contains between 0.5 and 50% water, for the purpose of producing $C_4$ alkenes, characterized in that it uses a catalyst that comprises at least one mesostructured material that comprises silicon.

Overall, the state of the art described above shows that, among the numerous solids studied for implementing the dehydration reaction of alcohols and the corresponding isomerization of formed alkenes in a simultaneous way, only the zeolites (for example, FER, TON) and the strongly acidified aluminas (sulfuric acid) have brought about a significant skeletal isomerization of the butenes that are formed. However, the aluminas that are used still remain much too weakly performing in terms of selectivity relative to the skeletal isomerization (certainly on the part of nature and the force of their acidity) and stability over time that is extensively perfectible. In addition, the zeolitic solids have serious drawbacks linked to the major Bronsted acidity that is developed and to certain crystalline structures that promote the secondary reactions and in particular the reactions of oligomerization, cracking and transfer of hydrogen. Let us recall also that the contact time of alkenes formed after dehydration of alcohols (accessibility to active sites and diffusion of molecules) is to be optimized in such a way as to implement the skeletal isomerization while limiting the secondary oligomerization reactions.

The applicant showed that the use of a catalyst comprising at least one silicon-based mesostructured material in a process for dehydration of a $C_4$ monoalcohol combined with the skeletal isomerization of the thus formed $C_4$ alkene made it possible to improve the catalytic performance levels in terms of selectivity of butene isomers, to increase the stability of the catalyst, and to increase the yield of $C_4$ isomers in comparison to other commonly used catalysts that do not contain the silicon-based mesostructured material.

Based on the methods of synthesis (subsequently described within the text of this invention), acidity properties that are suitable for these materials have been developed. Thus, it is possible to obtain a range of acidity that goes from a typical acidity of the one developed by the conventional amorphous mesoporous aluminosilicate solids to a higher acidity of zeolitic nature. These properties of specific acidity, which are intermediate between those of aluminum and zeolitic solid, are in part linked to the specificity of the mesostructuring of the material. The latter has many other advantages during the use of these solids as potential catalysts, such as, for example, a specific and even controlled diffusion of reagents and products from the reaction, an accessibility and a particular interaction of the reagents with active sites, very large active surface areas (combined with very high possible values of specific surface areas), and specific containment effects.

DETAILED DESCRIPTION OF THE INVENTION

This invention has as its object a process for simultaneous dehydration and skeletal isomerization of a feedstock that comprises at least one $C_4$ monoalcohol and that contains between 0.5 and 50% water, for the purpose of producing $C_4$ alkenes, with said process operating at a temperature of between 250 and 550° C., under a pressure of between 0.1 and 1 MPa, with an hourly volumetric flow rate of between 0.1 and 10 h-1, characterized in that it uses a catalyst that comprises at least one mesostructured material that comprises silicon and at least one element X that is selected from among aluminum, boron, gallium, indium and germanium.

Hourly volumetric flow rate, also designated by the term VVH, is defined as the ratio of the volumetric flow rate of feedstock in $m^3/h$ at 15° C., 1 atm per volume of catalyst.

In accordance with the invention, the feedstock comprises at least one $C_4$ monoalcohol, with said $C_4$ monoalcohol being selected from among 1-butanol, 2-butanol, isobutanol and tert-butanol, taken by itself or in a mixture. In a preferred way, the feedstock for the most part comprises isobutanol. For the most part means that the mass ratio of isobutanol to the other $C_4$ monoalcohols is greater than 50%, preferably greater than 70%, and more preferably greater than 80%.

In accordance with the invention, the feedstock can contain 0.5 to 50% by weight of water. It can also contain at most 10% by weight of impurities linked to methods for obtaining the feedstock (nitrogen, acids, aldehydes, non-$C_4$ alcohols, primarily).

The presence of water in the process, whether it is introduced with the feedstock or else with alcohol, or else whether it results from the dehydration reaction of alcohol, advantageously makes it possible to limit the oligomerization reactions, inevitable during the skeletal isomerization reaction, and therefore to improve the selectivity of the catalyst.

The concentration of water in the reactor is adjusted between 0.5% by weight relative to the alcohol and up to 50% by weight. Beyond this dilution, the process becomes difficult to justify in terms of energy. It will be possible to use a device of the type for mechanical recompression of vapors between the feedstock and the reactor or else in products for minimizing the energy consumption of the process.

In accordance with the invention, said process for simultaneous dehydration and skeletal isomerization is performed at a temperature of between 250 and 550° C., preferably between 300 and 450° C., under a pressure of between 0.1 and 1 MPa, preferably between 0.1 and 0.5 MPa, with an hourly volumetric flow rate of between 0.1 and 10 $h^{-1}$, preferably between 2 and 8 $h^{-1}$, and more preferably between 2 and 4 $h^{-1}$.

The reaction unit that is provided with catalyst can be used in a fixed bed and in a moving bed, preferably in an adiabatic fixed bed. The reaction is carried out in gaseous phase with upward or downward flow, in one/several reactors with reheating between each reaction stage that makes it possible to compensate for the overall endothermicity. To reduce the losses of feedstock in the reactor, radial reactor technologies are preferably used, where the catalyst is placed between vertical internals (grids or diffusers) and where the thickness of the catalyst layer through which the reactive fluid passes is minimized without thereby resorting to reactors with an atypical ratio between diameter and height (larger than 1). The catalyst is regenerated periodically. In the case of use in a fixed bed, said reaction unit alternatively carries out the reactions for the production of $C_4$ alkenes and the regeneration of said catalyst in such a way as to eliminate the coke that is deposited on the surface of said catalyst during said reactions. In the case of an alternative use in a moving bed, said catalyst can be transported between said reaction unit and a regeneration unit.

Description of the Silicon-Based Mesostructured Material Encompassed in the Catalyst Used According to the Invention A mesostructured material is an inorganic oxide solid that has particular textural and structural properties relative to other mesoporous inorganic oxide solids. Actually, if the mesostructured materials are also characterized by the presence of a mesoporosity, i.e., by the presence of pores having a size of between 1.5 and 50 nm according to IUPAC, this mesoporosity has quite specific characteristics since the mesopores have the special feature of having uniform morphology and dimensions and of being distributed periodically relative to one another. The mesopores thus form a "structured" network, hence the name of mesostructured solids that has been given to them. In a complementary way, the inorganic network constructed around this structured mesopore network is called a wall of mesostructured material. The mesostructures encountered are numerous: hexagonal 2D, vermicular, cubic 3D, lamellar, etc., and the range of the size of pores is wide since it sweeps the entire field of mesopores from 2 to 50 nm. In addition to this mesostructured porosity, these materials can also be characterized by the presence of micropores. The elementary particles that constitute these materials are therefore mesostructured and optionally microporous. The micropores, when they are present, are located in the wall of said mesostructured material. Said elementary particles consist of material in the sense where their successive aggregation and then their agglomeration will constitute the material in the form of a powder that can be used as is or shaped according to the well-known methods of one skilled in the art, as described below. Said elementary particles can have neither morphology nor specific size or else conversely have a particular shape and dimension, with these differences generally being a function of synthesis methodologies used. For example, said elementary particles can be spherical and be characterized by a diameter that is at best equal to 200 μm, with these specificities generally being attributed to a synthesis methodology involving a so-called atomization or aerosol process.

Preferably, the mesostructured material that comprises silicon and is encompassed in the catalyst that is used in the process according to the invention has a mesostructure that is hexagonal 2D, vermicular, or cubic 3D.

Preferably, said mesostructured material that comprises silicon consists of spherical elementary particles having a diameter that is less than or equal to 200 μm.

Said mesostructured material that comprises silicon advantageously has a specific surface area of between 100 and 1,200 $m^2/g$, in a very advantageous manner between 200 and 1,000 $m^2/g$, and in a very preferred manner between 300 and 1,000 $m^2/g$.

In this invention, we focus on mesostructured materials comprising the element silicon and more particularly mesostructured materials comprising silicon and developing acidity properties. Thus, in accordance with the invention, said mesostructured material comprises, in addition to silicon, at least one element X that is selected from among aluminum, boron, gallium, indium and germanium.

Preferably, said mesostructured material that comprises silicon comprises, in addition to silicon, at least the element aluminum and is therefore a mesostructured aluminosilicate material.

Said mesostructured material, comprising silicon and at least one element X that is selected from among aluminum, boron, gallium, indium and germanium, preferably aluminum, has an Si/X molar ratio of between 0.05 and 1,000, preferably between 0.05 and 6 or between 15 and 1,000, and in an even more preferred way between 0.05 and 3 or between 15 and 100.

Preferably, the mesostructured material that comprises silicon and is encompassed in the catalyst that is used in the process according to the invention comprises proto-zeolitic entities and/or zeolitic entities in the wall of said mesostructured material. In an even more preferred way, said mesostructured material that comprises silicon comprises proto-zeolitic entities in the wall of said mesostructured material.

The developed acidity properties are specific to these materials. The developed acidity range goes from a typical acidity of the one developed by conventional amorphous mesoporous aluminosilicate solids to a much stronger acidity of zeolitic nature. These properties of acidity, intermediate to those of aluminum and zeolitic solids, are linked to the presence of the element X, preferably aluminum, in said mesostructured material that comprises silicon. Acidity properties are defined in this text as an acidity that is for the most part of the Bronsted acid type, i.e., an acidity of protonic nature.

The specificity of the developed acidity can be connected to the very large number of acid sites that can be contained in these materials owing to the very large values of specific surface areas that can be reached.

Said acidity, in particular when it approaches the acidity developed by zeolites, can be connected to the presence of proto-zeolitic entities and/or zeolitic entities in the wall of said mesostructured material. Said wall can then be respectively amorphous and/or crystallized. The expression amorphous and crystallized is defined as the wall being able to be characterized by a mixture of amorphous zones, combined with the presence of proto-zeolitic entities, and crystallized zones, combined with the presence of zeolitic entities. More specifically, the proto-zeolitic entities are radicals prepared from reagents used for the synthesis of zeolites, with the preparation of said radicals not having been conducted until the stage of the formation of crystallized zeolites. The result is that said proto-zeolitic entities, of small size, are not detected when they are characterized by high-angle X-ray diffraction and therefore lead to amorphous walls or wall zones. Likewise, the zeolitic entities are radicals prepared from reagents used for the synthesis of zeolites, the preparation of said radicals having been conducted up to the stage of formation of crystallized zeolites. They therefore lead to crystallized walls or wall zones. Let us specify that said proto-zeolitic or zeolitic entities comprise the element silicon and at least one element X, with X preferably being aluminum. In this case, the element X, preferably aluminum, is located in the wall of said mesostructured material.

An acidity of zeolitic nature can also be introduced by incorporation of zeolite nanocrystals in said mesostructured material. Said nanocrystals then are not constituent elements of the wall of the mesostructured material but are trapped within the unit constituted by the inorganic wall and the structured mesopore network of said mesostructured material. In this case, the element X, preferably aluminum, can be located in said zeolite nanocrystals and/or the wall of said mesostructured material.

Preferably, the proto-zeolitic entities are radicals for initiating at least one zeolite that is selected from among the following zeolites: ZSM-5, ZSM-48, ZSM-22, ZSM-23, ZBM-30, EU-2, EU-11, silicalite, beta, zeolite A, faujasite, Y, USY, VUSY, SDUSY, mordenite, NU-10, NU-87, NU-88, NU-86, NU-85, IM-5, IM-12, theta-1, ferrierite and EU-1. In a preferred manner, the proto-zeolitic entities are radicals for initiating at least one zeolite that is selected from among the zeolites of structural types MFI, FER, BEA, FAU, LTA and TON.

Preferably, the zeolitic entities and the zeolite nanocrystals are selected from among the following zeolites: ZSM-5, ZSM-48, ZSM-22, ZSM-23, ZBM-30, EU-2, EU-11, silicalite, beta, zeolite A, faujasite, Y, USY, VUSY, SDUSY, mordenite, NU-10, NU-87, NU-88, NU-86, NU-85, IM-5, IM-12, theta-1, ferrierite and EU-1. In a very preferred manner, the zeolitic entities and the zeolite nanocrystals are selected from among the zeolites of structural types MFI, FER, BEA, FAU, LTA and TON.

Preferably, the catalyst according to the invention consists integrally of silicon-based mesostructured material.

The mesostructured material encompassed in the catalyst that is used in the process according to the invention is characterized by several techniques of analyses and in particular by low-angle X-ray diffraction and optionally high-angle X-ray diffraction (low-angle XRD, high-angle XRD), by nitrogen volumetric analysis (BET), by transmission electron microscopy (TEM), by scanning electronic microscopy (SEM), and by X fluorescence (XF).

The low-angle X-ray diffraction technique (values of angle $2\theta$ encompassed between 0.5 and 3°) makes it possible to characterize the periodicity on the nanometric scale generated by the mesostructure of the material. The X-ray analysis is done on powder with a diffractometer operating by reflection and equipped with a rear monochromator by using the radiation of copper (wavelength of 1.5406 Å). The peaks that are usually observed on the diffractograms corresponding to a given value of the angle $2\theta$ are combined with interreticular distances $d_{(hkl)}$ that are characteristic of the structural symmetry of the material, ((hkl) being the Miller indices of the reciprocal network) by Bragg's equation: $2 d_{(hkl)}*\sin(\theta)=\eta*\lambda$. This indexing then makes it possible to determine mesh parameters (abc) of the direct network, with the value of these parameters being based on the hexagonal, cubic or vermicular structure that is obtained.

The high-angle X-ray diffraction technique (values of angle $2\theta$ encompassed between 5 and 70°) makes it possible to characterize a crystallized solid that is defined by the repetition of an individual pattern or an elementary mesh on the molecular scale. As for the low-angle X-ray diffraction, the peaks observed on the diffractograms that correspond to a given value of the angle $2\theta$ are combined with interreticular distances $d_{(hkl)}$ that are characteristic of the structural symmetry(ies) of the material, ((hkl) being the Miller indices of the reciprocal network) by Bragg's equation: $2 d_{(hkl)}*\sin(\theta)=\eta*\lambda$. This indexing then makes it possible to determine mesh parameters (abc) of the direct network. The high-angle XRD analysis is therefore suitable for the structural characterization of the constituent zeolitic entities of crystallized walls. In particular, it makes it possible to access the diameter of micropores of the zeolitic entities. The value of the angle obtained on the XR diffractogram makes it possible to get back to the correlation distance d according to Bragg's law: $2d*\sin(\theta)=\eta*\lambda$.

The nitrogen volumetric analysis that corresponds to the physical adsorption of nitrogen molecules in the porosity of the material via a gradual increase in the pressure at constant temperature gives information about the particular textural characteristics (diameter of the mesopores, type of porosity, specific surface area) of the material. In particular, it makes it possible to access the total value of the mesopore volume (see micropore and mesopore) of the material. The diameter of the mesopores reported in the examples corresponds to the diameter obtained from the desorption branch of the isotherm. The difference between the value of this diameter $\phi$ and the correlation distance between mesopores d defined by low-angle XRD as described above makes it possible to access the value e where $e=d-\phi$ and is characteristic of the thickness of the walls of the material.

The analysis by transmission electron microscopy (TEM) is a technique that is also extensively used for characterizing the mesostructure of the material. The TEM makes possible the formation of an image of the solid that is studied, with the observed contrasts being characteristic of the structural organization, the texture, the morphology or else the chemical composition of the observed particles, with the resolution of the technique reaching a maximum of 0.2 nm. The TEM photos are made from microtome cross-sections of the sample. The analysis of the image also makes it possible to access parameters d, $\phi$ and e that are characteristic of the mesostructure defined above.

The morphology of the elementary particles has been established by analysis of photos obtained by scanning electronic microscopy (SEM).

The overall composition of the material is determined by X fluorescence (XF).

Process for Preparation of a Silicon-Based Mesostructured Material Encompassed in the Catalyst that is Used According to the Invention.

Any process, known to one skilled in the art, for synthesis of mesostructured material comprising silicon and developing acidity properties as developed in this invention is suitable for preparing said silicon-based mesostructured material encompassed in the catalyst used according to the invention.

In a general way, the mesostructured materials are conventionally obtained via synthesis methods called soft chemistry that consist in bringing inorganic precursors, in aqueous solution or in polar solvents, into the presence of ionic or neutral structuring agents, generally molecular or macromolecular surfactants. The formation of material results from favorable interactions between the inorganic walls during the formation (hydrolysis/condensation of the inorganic precursors) and the micellar phase formed by said surfactants. This mesostructuring phenomenon results from quite specific operating conditions, for example in terms of concentration of reagents, pH, and temperature, and it leads to the formation of an organic-inorganic hybrid solid that consists of a micellar mesophase (hexagonal 2D, cubic 3D, vermicular, etc.) trapped in an inorganic matrix. Owing to the concentration c of surfactant, two mechanisms for formation of mesostructured materials are proposed. When c is much higher than the CMC (Critical Micellar Concentration: concentration starting from which the micellar phase forms spontaneously), a micellar mesophase is initially formed and the final solid results from the hydrolysis/condensation of the inorganic precursors around the latter. This mechanism is called "True Liquid Crystal Templating." Conversely, when c is close to CMC, the mesostructuring occurs via a cooperative self-assembly mechanism between the inorganic precursors and the molecules or macromolecules of surfactant. In this latter case, the hydrolysis/condensation of the inorganic precursors, the micellar self-assembly, and the development of favorable interactions between these elements took place simultaneously, with the related syntheses employing conventional stages, for example of precipitation, and curing by autoclaving. This self-assembly can also be carried out by gradual evaporation of a solution of these reagents whose concentration in structuring agent c is less than CMC, which leads either to the formation of mesostructured films in the case of a deposit on substrate ("dip-coating" technique) or to the formation of mesostructured monoliths in the case of evaporation in a given morphology container, or to the formation of a mesostructured powder after atomization of the solution (aerosol technique). By way of example, the U.S. Pat. No. 6,387,453 discloses the formation of mesostructured organic-inorganic hybrid films by the "dip-coating" technique, these same authors further having used the aerosol technique for developing purely silicic mesostructured materials (C. J. Brinker, Y. Lu, A. Sellinger, H. Fan, *Adv. Mater.*, 1999, 11, 7). Self-assembly by gradual evaporation is a method called "EISA" for "Evaporation-Induced Self-Assembly."

The removal of the pores is next achieved by elimination of the surfactant, the latter being conventionally implemented by chemical extraction processes or by heat treatment. Based on the nature of the inorganic precursors and the structuring agent used as well as the operating conditions imposed, several families of mesostructured materials have been developed, such as the family of the M41S (including the solids called MCM-41) that is obtained via the use of long-chain quaternary ammonium salts as structuring agents (J. S. Beck, J. C. Vartuli, W. J. Roth, M. E. Leonowicz, C. T. Kresge, K. D. Schmitt, C. T.-W. Chu, D. H. Olson, E. W. Sheppard, S. B. McCullen, J. B. Higgins, J. L. Schlenker, *J. Am. Chem. Soc.*, 1992, 114, 27, 10834) or else the family of SBA (including the solids called SBA-15) obtained via the use of three-block copolymers as structuring agents (D. Zhao, J. Feng, Q. Huo, N. Melosh, G. H. Fredickson, B. F. Chmelka, G. D. Stucky, *Science*, 1998, 279, 548).

Obtaining a mesostructured material comprising silicon and developing acidity properties as developed in this invention, i.e., comprising in addition to silicon at least one element X, with X preferably being aluminum, can be carried out according to the synthesis methodologies described above by using silicic inorganic precursors and inorganic precursors of element X, with X preferably being aluminum. It is also possible to introduce or to reintroduce the element X after formation of the organic-inorganic hybrid solid, consisting of a micellar mesophase (hexagonal 2D, cubic 3D, vermicular, etc.) trapped in an inorganic matrix, obtained after the synthesis stages inducing the mesostructuring phenomenon, and precursor of the mesostructured material comprising silicon. To do this, any technique for modification of the surface that is well known to one skilled in the art, such as the grafting of at least one precursor of at least one element X, dry impregnation of at least one precursor of at least one element X, and excess impregnation of at least one precursor of at least one element X can be used.

Preferably, the mesostructured material comprising silicon and encompassed in the catalyst that is used in the process according to the invention is obtained by the "EISA" method. In an even more preferred way, the mesostructured material comprising silicon and encompassed in the catalyst that is used in the process according to the invention is obtained by the aerosol technique or else atomization technique or else spray-drying technique.

Aluminosilicate mesostructured materials obtained by aerosol means are perfectly described in the patents FR 2,872,151, FR 2,872,152 and FR 2,886,637.

The possible presence in the mesostructured material comprising silicon and encompassed in the catalyst that is used in the process according to the invention of proto-zeolitic entities and/or zeolitic entities is carried out via all of the synthesis methods that are known to one skilled in the art making it possible to constitute a wall of said mesostructured material from said proto-zeolitic entities and/or zeolitic entities.

In a general way, the proto-zeolitic entities are radicals resulting from bringing said radicals—which can be used for initiating the synthesis of any zeolite that is known to one skilled in the art, and, in particular, but in a non-exhaustive way, in the synthesis of zeolites listed in "*The Atlas of Zeolite Framework Types,*" 5$^{th}$ Revised Edition, 2001, C. Baerlocher, W. M. Meier, D. H. Olson—into the presence of at least one structuring agent, at least one silicic precursor, and at least one precursor of at least one element X that is selected from among aluminum, boron, indium, gallium and germanium, preferably aluminum, under variable conditions of time and temperature making it possible to result in a clear solution.

Likewise, any zeolite and, in particular, but in a non-exhaustive way, those listed in the "*Atlas of Zeolite Framework Types,*" 5$^{th}$ Revised Edition, 2001, C. Baerlocher, W.

M. Meier, D. H. Olson can be used for the formation of zeolitic entities and zeolite nanocrystals.

In particular, the operating procedures for synthesis of a mesostructured material obtained by aerosol means and comprising proto-zeolitic entities and/or zeolitic entities in the wall of said mesostructured material are perfectly described in the patents FR 2,920,756 and FR 2,920,757. Likewise, numerous references to operating procedures of solids of this type via other synthesis methodologies are listed there. In addition, the operating procedures by aerosol means making possible the incorporation of zeolite nanocrystals, as described in the part "Description of Silicon-Based Mesostructured Material Encompassed in the Catalyst Used According to the Invention" of this invention are described in the patents FR 2,872,152 and FR 2,886,637.

The organic-inorganic hybrid solid, consisting of a micellar mesophase (hexagonal 2D, cubic 3D, vermicular, etc.) trapped in an inorganic matrix, obtained after the synthesis stages inducing the mesostructuring phenomenon, and precursor of the mesostructured material comprising silicon, usually occurs after optional stages of filtering and washing, in the form of a powder.

The elimination of the organic fraction, and therefore the removal of the pores, is advantageously carried out by chemical extraction processes or by heat treatment and preferably by calcination in air in a temperature range of 300 to 1,000° C., and preferably in a range of 400 to 600° C. for a period of 1 to 24 hours, and in a preferred way for a period of 2 to 12 hours. This elimination can be done before or after the optional shaping stages.

The mesostructured material comprising silicon encompassed in the catalyst that is used in the process according to the invention can be shaped by any technique that is known to one skilled in the art. The shaping can be done by, for example, extrusion, by tabletting, by pelletizing, by pelletizing and crushing, by drying, by atomization, by the drop (oil-drop) coagulation method, by turntable granulation or by any other method that is well known to one skilled in the art. Furthermore, said mesostructured material may have been treated as is well known by one skilled in the art by additives for facilitating the shaping and/or improving the final mechanical properties of said catalyst. By way of example of additives, it is possible to cite in particular cellulose, carboxymethyl cellulose, carboxyethyl cellulose, xanthan gums, surfactants, flocculating agents such as polyacrylamides, carbon black, starches, stearic acid, polyacrylic alcohol, polyvinyl alcohol, biopolymers, glucose, polyethylene glycols, etc.

Said mesostructured material that comprises silicon comes in the form of spheres, spheroids, pellets or extrudates, preferably extrudates. In a very advantageous manner, said material comes in the form of extrudates with a diameter of between 0.5 and 5 mm and more particularly between 0.7 and 2.5 mm. The shapes of said extrudates can be cylindrical (which may or may not be hollow), braided cylindrical, multilobe (2, 3, 4, or 5 lobes, for example), or rings. The cylindrical and multilobe shapes are used in a preferred manner, but any other shape can be used.

It is also possible to add other components to said mesostructured material that comprises silicon in such a way as to form the catalyst that is used according to the invention, with these components able to be introduced during shaping stages described above. Said components can be, in a non-exhaustive way, at least one porous oxide material that is selected from the group that is formed by alumina, silica, magnesia, clays, titanium oxide, zirconium oxide, lanthanum oxide, cerium oxide, aluminum phosphates, boron phosphates, and a mixture of at least two of the oxides cited above. Said porous oxide material can also be selected from among the mixtures of alumina-boron oxide, alumna-titanium oxide, alumina-zirconia, and titanium oxide-zirconia. The aluminates, for example the aluminates of magnesium, calcium, barium, manganese, iron, cobalt, nickel, copper and zinc, as well as the mixed aluminates, for example those containing at least two of the metals cited above, are advantageously used as porous oxide material. It is also possible to use titanates, for example titanates of zinc, nickel, and cobalt. It is also advantageously possible to use mixtures of alumina and silica and mixtures of alumina with other compounds such as the elements of group VIB, phosphorus, fluorine or boron. It is also possible to use clays that are simple, synthetic or natural, of the type dioctahedral phyllosilicate 2:1 or trioctahedral phyllosilicate 3:1, such as kaolinite, antigorite, chrysotile, montmorillonnite, beidellite, vermiculite, talc, hectorite, saponite, and laponite. These clays optionally can be delaminated. It is also advantageously possible to use mixtures of alumina and clay and mixtures of aluminosilicate and clay. Likewise, it is possible to use at least one compound that is selected from the group that is formed by the family of molecular sieves of the crystallized aluminosilicate type and synthetic and natural zeolites such as the A zeolite, the Y zeolite, the fluorinated Y zeolite, the Y zeolite containing rare earths, USY, VUSY, SDUSY, the X zeolite, the L zeolite, the beta zeolite, the small-pore mordenite, the large-pore mordenite, and the following zeolites: omega, NU-10, ZSM-22, NU-85, NU-86, NU-87, NU-88, ferrierite, ZSM-5, ZSM-48, ZSM-23, ZBM-30, EU-2, EU-11, silicalite, IM-5, IM-12, and EU-1. Among the zeolites, it is usually preferred to use zeolites whose ratio of silicon/aluminum (Si/Al) framework atoms is greater than approximately 3/1. Advantageously, zeolites of faujasite structure and in particular stabilized and ultrastabilized Y zeolites (USY) are used either in the form at least partially exchanged with metal cations, for example cations of the alkaline-earth metals and/or cations of rare earth metals of atomic numbers 57 to 71 inclusive, or in hydrogen form (Atlas of Zeolite Framework Types, 6$^{th}$ Revised Edition, 2007, Ch. Baerlocher, L. B. McCusker, D. H. Olson). Finally, as a porous oxide material, it is possible to use at least one compound that is selected from the group that is formed by the family of non-crystallized aluminosilicate-type molecular sieves, such as the mesoporous silicas, the silicalite, the silicoaluminophosphates, the aluminophosphates, the ferrosilicates, the titanium silicoaluminates, the borosilicates, the chromosilicates, and the aluminophosphates of transition metals (including cobalt). The various mixtures that use at least two of the compounds cited above are also suitable.

The specific acidity properties of the mesostructured material comprising silicon and encompassed in the catalyst that is used in the process according to the invention can also be adapted by adding one or more heat post-treatment stages (calcination), by chemical and/or hydrothermal means, to the synthesis stages mentioned above.

When said mesostructured material that comprises silicon comprises zeolitic entities and/or zeolite nanocrystals introduced by incorporation, this post-treatment is a hydrothermal treatment and/or by chemical means usually used to carry out the dealuminification of solids of zeolitic nature. This optional stage can be carried out by any method that is known to one skilled in the art (refer to, for example, "Hydrocracking Science and Technology" by J. Scherzer and A. J. Gruia, Marcel Dekker, Inc., 1996).

The calcination is preferably done in the presence of molecular oxygen, for example by carrying out a flushing with air, at a temperature that is less than or equal to 1100° C. This treatment, for example, can be done in a flushed bed, in a swept bed or under static atmosphere. For example, the furnace that is used can be a rotary kiln or a vertical furnace with radial flushed layers. The conditions of calcination, temperature and duration depend primarily on the maximum temperature of use of the catalyst, with the preferred calcination conditions being between more than one hour at 200° C. and less than one hour at 1100° C., preferably between 300 and 600° C. for a period of 1 to 24 hours and in a more preferred way for a period of 2 to 12 hours. The calcination can be performed in the presence of water vapor. The final calcination can optionally be done in the presence of an acidic or basic vapor. For example, the calcination can be done under partial pressure of ammonia.

The hydrothermal treatments are done by any technique that is known to one skilled in the art. Hydrothermal treatment is defined as bringing into contact—at any stage of development—the solid with water in the vapor phase or liquid phase. Hydrothermal treatment can be defined in particular as curing, steaming (steam treatment), autoclaving, calcination in moist air, and rehydration. In a preferred manner, the hydrothermal treatment is done by steaming (steam treatment) in a furnace in the presence of water vapor. The temperature during the steaming (steam treatment) can be between 300 and 1100° C., and preferably greater than 700° C. for a period of time of between 30 minutes and 12 hours, and preferably between 30 minutes and 4 hours. The water vapor content is higher than 20 g of water per kg of dry air, and preferably greater than 40 g of water per kg of dry air, and in a preferred manner greater than 100 g of water per kg of dry air. Such a treatment can, if necessary, replace the calcination treatment totally or partially.

The solid can also advantageously be subjected to a hydrothermal treatment in a contained atmosphere. Hydrothermal treatment in a contained atmosphere is defined as a treatment of running through the autoclave in the presence of water under a temperature that is higher than ambient temperature. The temperature during autoclaving can be between 100 and 250° C. for a period of time of between 30 minutes and 6 hours, preferably between 30 minutes and 2 hours.

The entire disclosures of all applications, patents and publications, cited herein and of corresponding application No. 12/00.950 FR, filed Mar. 29, 2012 are incorporated by reference herein.

EXAMPLES

Example 1

Synthesis of Catalyst Based on an Al-SBA-15-Type Mesostructured Aluminosilicate Material with an Si/Al Molar Ratio=75 Obtained by Precipitation and Autoclaving According to the Operating Procedure Described by D. Zhao, J. Feng, Q. Huo, N. Melosh, G. H. Fredickson, B. F. Chmelka, G. D. Stucky, Science, 1998, 279, 548, M1

8.04 g of surfactant P123 (three-block copolymer: $[EO]_{20}$-$[PO]_{70}$-$[EO]_{20}$ with EO:ethylene polyoxide and PO:propylene polyoxide) is added to 300 ml of an HCl solution at pH=2. The whole mixture is kept stirred for 24 hours at a temperature of 40° C. 16.64 g of tetraethyl orthosilicate (TEOS) is then added. The whole mixture is again stirred for 24 hours at a temperature of 40° C. 0.26 g of aluminum tert-butoxide $Al(O^tBu)_3$ is then added. The whole mixture is again kept stirred for 24 hours at a temperature of 40° C. The whole mixture is then placed in a 500-ml autoclave with a Teflon casing. The whole mixture is then placed in a ventilated oven at a temperature of 100° C. for 24 hours. After curing in an autoclave, the suspension is filtered, and then the solid is dried for 24 hours in a ventilated oven at a temperature of 100° C. The solid is finally steamed at 550° C. for 4 hours, and then steamed at 650° C. for 2 hours in the presence of water vapor.

The solid is characterized by low-angle XRD, by nitrogen adsorption isotherm; by TEM, and by X fluorescence. The TEM analysis shows that the final material has a mesostructured porosity that is characterized by a 2D hexagonal structure. The nitrogen adsorption isotherm analysis leads to a specific surface area of the final material of $S_{BET}$=447 m$^2$/g and a mesoporous diameter of $\phi$=5.1 nm. The small-angle XRD analysis leads to the display of three correlation peaks at angles 2θ=0.9, 1.6 and 1.8. Bragg's equation 2 d*sin (1.2)= 1.5406 makes it possible to calculate the distance d for correlation between the pores of the mesostructured matrix, or d=10.5 nm. The thickness of the walls of the mesostructured material defined by e=d−$\phi$ is therefore e=5.4 nm. A SEM picture of the elementary particles thus obtained indicates that these particles do not have defined morphology. The Si:Al molar ratio=75 is provided by the XF analysis.

Example 2

Synthesis of the Catalyst Based on an Al-MCM-41-Type Mesostructured Aluminosilicate Material of the Si/Al Molar Ratio=10 Obtained by Aerosol According to the Operating Procedure Described by the Patent FR 2,872,151, M2

0.47 g of aluminum trichloride is added to a solution that contains 30 g of ethanol, 14.5 ml of water, 0.036 ml of HCl, and 1.4 g of surfactant CTAB (cetyltrimethylammonium bromide $(CH_3(CH_2)_{15}N(CH_3)_3{}^+Br^-)$. The whole mixture is left to stir at ambient temperature until the aluminum precursor is completely dissolved. 4.09 g of tetraethyl orthosilicate (TEOS) is then added. After stirring for 10 minutes at ambient temperature, the whole mixture is sent into the atomization chamber of an aerosol generator, and the solution is sprayed in the form of fine droplets under the action of the carrier gas (dry air) that is introduced under pressure (P=1.5 bar). The droplets are dried according to aerosol technology. The temperature of the drying oven is set at 350° C. The recovered powder is then calcined in air for 5 hours at T=550° C. The solid is characterized by low-angle XRD, by nitrogen adsorption isotherm, by TEM, and by X fluorescence. The TEM analysis shows that the final material has a mesostructured porosity that is characterized by a vermicular structure. The nitrogen adsorption isotherm analysis leads to a specific surface area of the final material of $S_{BET}$=800 m$^2$/g and to a mesopore diameter of $\phi$=2.4 nm. The small-angle XRD analysis leads to the display of a correlation peak at the angle 2θ=2.4. Bragg's equation 2 d*sin(1.2)=1.5406 makes it possible to calculate the distance d for correlation between the mesopores of the material or d=3.7 nm. The thickness of the walls of the mesostructured material defined by e=d−$\phi$ is therefore e=1.3 nm. A SEM picture of the elementary particles indicates that these particles have a particular spherical morphology. The Si:Al molar ratio=10 is provided by the XF analysis.

Example 3

Synthesis of the Catalyst Based on a Mesostructured Aluminosilicate Material of the Type Whose Wall Contains ZSM-5 (MFI)-Type Aluminosilicate Proto-Zeolitic Entities Such as the Si/Al Molar Ratio=59 that is Obtained by Aerosol According to the Operating Procedure Described by the Patent FR 2,920,756, M3

6.86 g of a tetrapropylammonium hydroxide solution (TPAOH: 40% by mass in an aqueous solution) is added to 0.37 g of aluminum sec-butoxide ($Al(O^SC_4H_9)_3$). After 30 minutes while being stirred vigorously at ambient temperature, 27 g of demineralized water and 18.75 g of tetraethyl orthosilicate (TEOS) are added. The entire mixture is left under vigorous stifling at ambient temperature for 18 hours in such a way as to obtain a clear solution. To this solution is then added a solution that contains 66.61 g of ethanol, 61.24 g of water, and 5.73 g of surfactant F127 (three-block copolymer: $[EO]_{64}$-$[PO]_{100}$-$[EO]_{64}$ with EO:ethylene polyoxide and PO:propylene polyoxide) (pH of the mixture=13.5). The entire mixture is left to stir for 10 minutes. The whole mixture is sent into the atomization chamber of an aerosol generator, and the solution is sprayed in the form of fine droplets under the action of the carrier gas (dry air) that is introduced under pressure (P=1.5 bar). The droplets are dried according to the aerosol technology. They are then introduced into a furnace that is regulated at a drying temperature that is set at 350° C. The recovered powder is then dried for 18 hours in the oven at 95° C. The powder is then calcined in air for 5 hours at 550° C. The solid is characterized by low-angle XRD, by nitrogen volumetric analysis, by TEM, by SEM, and by XF. The TEM analysis shows that the final material has a mesostructured porosity that is characterized by a vermicular structure. The nitrogen volumetric analysis leads to a value of the micropore volume $V_{micro}$ ($N_2$) of 0.13 ml/g, a value of the mesopore volume $V_{meso}$ ($N_2$) of 0.61 ml/g, and a specific surface area of the final material of S=781 m²/g. The mesopore diameter $\phi$ is 7 nm. The small-angle XRD analysis leads to the display of a correlation peak at the angle $2\theta=0.78°$. Bragg's equation $2 d^*\sin(\theta)=1.5406$ makes it possible to calculate the distance d for correlation between the mesopores of the material, or d=11.3 nm. The thickness of the walls of the material that is defined by $e=d-\phi$ is therefore e=4.3 nm.

A SEM picture of the elementary particles indicates that these particles have a particular spherical morphology. The Si/Al molar ratio=10 is provided by XF analysis.

Example 4

Dehydration/Isomerization Activity of Isobutanol on the Catalysts According to Examples 1 to 3

A flow rate of commercial isobutanol that contains 0.5% by weight of water is injected so as to reach the targeted hourly volumetric flow rate. At the outlet of the reactor, all of the effluent is analyzed by on-line injection by gas phase chromatography. With the online analyst being equipped with an FID detector, the quantification of hydrogen, CO or $CO_2$ that is possibly formed is not made possible. However, the possible dehydrogenation reactions are followed thanks to the analysis of the isobutyraldehyde that is produced. The chromatographic method that is used makes possible the separation of isomers from butene and the identification of oxidized molecules that are formed. The reaction conditions that are involved are: a temperature of 350 or 400° C., with the reactor being isothermal, and a pressure of 0.1 bar relative and a vvh of 2 or 8 $h^{-1}$.

The hydrocarbon portion of the effluent for the most part contains all of the isomers of the butenes, and traces of propylene, and $C_1$, $C_2$ $C_3$, $C_5$ and $C_6$ hydrocarbons. The oxidized products that are formed (minority products) are: the dehydrogenation product (isobutyraldehyde) and diisobutyl ether (traces). The unconverted isobutanol is also analyzed. The results are presented in Tables 1 to 3. Only the majority compounds are reported, several minority radicals that are representative of the secondary reactions taking place (cracking, hydrogen transfer).

TABLE 1

(According to Example 1)

| | | Effluent Time under Load | | | | |
|---|---|---|---|---|---|---|
| Catalyst M1 | Feed-stock | 10 Hours | 25 Hours | 40 Hours | 55 Hours | Return Point 70 Hours |
| Temperature (° C.) | | 350 | 350 | 400 | 400 | 350 |
| vvh ($h^{-1}$) | | 2 | 8 | 2 | 8 | 2 |
| % Radical | | | | | | |
| Propane | | 0.02 | 0.01 | 0.1 | 0.05 | 0.015 |
| Propylene | | 0.2 | 0 | 0.2 | 0.1 | 0.1 |
| Isobutane | | 0.4 | 0.2 | 0.5 | 0.2 | 0.35 |
| Butene-2-trans | | 11.3 | 11.1 | 15.1 | 13.3 | 10.9 |
| Butene-1 | | 4.6 | 4.3 | 7.8 | 7.15 | 3.98 |
| Isobutene | | 70.5 | 72.2 | 59.9 | 65.2 | 72.3 |
| Butene-2-cis | | 9.8 | 9.6 | 11.9 | 9.65 | 9.4 |
| C5+ Sum | | 2.7 | 2.25 | 4.4 | 4.05 | 2.45 |
| Iso-butyraldehyde | | 0.2 | 0.12 | 0.01 | 0.1 | 0.15 |
| Butanone | | 0.06 | 0 | 0 | 0.01 | 0.1 |
| Isobutanol | 100 | 0.1 | 0.2 | 0 | 0.05 | 0.2 |
| Sum | | 99.88 | 99.98 | 99.91 | 99.86 | 99.95 |
| Conversion | | 99.9 | 99.5 | 100 | 99.8 | 99.9 |
| Selectivity of Linear Butenes in the C4 Olefins Fraction (%) | | 26.72 | 25.72 | 36.75 | 31.58 | 25.14 |
| C5+ Selectivity (%) | | 1.75 | 1.3 | 2.75 | 2.0 | 1.7 |
| Butenes Selectivity (%) | | 97 | 97.9 | 95.9 | 96.9 | 97.5 |

TABLE 2

(According to Example 2)

| | | Effluent Time under Load | | | | |
|---|---|---|---|---|---|---|
| Catalyst M2 | Feed-stock | 10 Hours | 25 Hours | 40 Hours | 55 Hours | Return Point 70 Hours |
| Temperature (° C.) | | 350 | 350 | 400 | 400 | 350 |
| vvh ($h^{-1}$) | | 2 | 8 | 2 | 8 | 2 |

TABLE 2-continued (According to Example 2)

| Catalyst M2 | Feed-stock | Effluent Time under Load | | | | |
|---|---|---|---|---|---|---|
| | | 10 Hours | 25 Hours | 40 Hours | 55 Hours | Return Point 70 Hours |
| % Radical | | | | | | |
| Propane | | 0.15 | 0.1 | 0.8 | 0.5 | 0.1 |
| Propylene | | 0.01 | 0.01 | 0.015 | 0.01 | 0.01 |
| Isobutane | | 0.25 | 0.15 | 0.5 | 0.3 | 0.35 |
| Butene-2-trans | | 14.3 | 13.8 | 16.5 | 15.2 | 14.1 |
| Butene-1 | | 5.8 | 4.68 | 7.1 | 5.9 | 5.5 |
| Isobutene | | 62.6 | 65.5 | 54.1 | 60.1 | 63.4 |
| Butene-2-cis | | 11.8 | 10.9 | 13.9 | 12.1 | 11.4 |
| C5+ Sum | | 4.8 | 4.1 | 6.6 | 5.8 | 4.2 |
| Iso-butyraldehyde | | 0.18 | 0.18 | 0.2 | 0.15 | 0.12 |
| Butanone | | 0.01 | 0.02 | 0.02 | 0.02 | 0.01 |
| Isobutanol | 100 | 0.1 | 0.26 | 0 | 0 | 0.7 |
| Sum | | 100 | 99.7 | 99.74 | 100.08 | 99.89 |
| Conversion | | 99.9 | 99.5 | 100 | 99.8 | 99.9 |
| Selectivity of Linear Butenes in the C4 Olefins Fraction (%) | | 33.76 | 30.97 | 40.94 | 35.58 | 32.84 |
| C5+ Selectivity (%) | | 4.80 | 4.12 | 6.60 | 5.81 | 4.20 |
| Butenes Selectivity (%) | | 94.5 | 94.88 | 91.6 | 93.3 | 94.4 |

TABLE 3

(According to Example 3)

| Catalyst M3' | Feed-stock | Effluent Time under Load | | | | |
|---|---|---|---|---|---|---|
| | | 10 Hours | 25 Hours | 40 Hours | 55 Hours | Return Point 70 Hours |
| Temperature (°C) | | 350 | 350 | 400 | 400 | 350 |
| vvh (h$^{-1}$) | | 2 | 8 | 2 | 8 | 2 |
| % Radical | | | | | | |
| Propane | | 0.04 | 0.01 | 0.1 | 0.05 | 0.03 |
| Propylene | | 0.1 | 0 | 0.15 | 0.1 | 0.05 |
| Isobutane | | 0.3 | 0.15 | 0.4 | 0.3 | 0.25 |
| Butene-2-trans | | 12.1 | 11.05 | 15.6 | 13.8 | 10.3 |
| Butene-1 | | 5.2 | 4.3 | 7.6 | 6.5 | 3.55 |
| Isobutene | | 68.1 | 71 | 58.3 | 63.5 | 73.9 |
| Butene-2-cis | | 10.5 | 10.1 | 12.2 | 11.2 | 9.1 |
| C5+ Sum | | 3.5 | 3.05 | 5.5 | 4.3 | 2.3 |
| Iso-butyraldehyde | | 0.1 | 0.1 | 0.01 | 0.1 | 0.15 |
| Butanone | | 0.01 | 0 | 0 | 0.01 | 0.1 |
| Isobutanol | 100 | 0.05 | 0.2 | 0.1 | 0.1 | 0.2 |
| Sum | | 100 | 99.96 | 99.96 | 99.96 | 99.93 |
| Conversion | | 99.9 | 99.5 | 100 | 99.8 | 99.9 |
| Selectivity of Linear Butenes in the C4 Olefins Fraction (%) | | 28.99 | 26.39 | 37.78 | 33.16 | 23.70 |
| C5+ Selectivity (%) | | 3.50 | 3.07 | 5.50 | 4.31 | 2.30 |

TABLE 3-continued (According to Example 3)

| Catalyst M3' | Feed-stock | Effluent Time under Load | | | | |
|---|---|---|---|---|---|---|
| | | 10 Hours | 25 Hours | 40 Hours | 55 Hours | Return Point 70 Hours |
| Butenes Selectivity (%) | | 95.9 | 96.45 | 93.7 | 95 | 96.85 |

The solids according to the invention therefore show good stability and good selectivity in isomers of the butenes. The secondary reactions that bring about the formation of $C_5^+$ oligomers are greatly limited.

The invention claimed is:

1. A process for a simultaneous dehydration and skeletal isomerization of $C_4$ monoalcohols to $C_4$ alkenes comprising:
    directing a feedstock comprising at least one $C_4$ monoalcohol and between 0.5 and 50 wt % of water to a reactor in the presence of a catalyst to perform the simultaneous dehydration and skeletal isomerization reaction and recovering an effluent comprising $C_4$ alkenes wherein:
    the reaction conditions comprise a temperature between 250 and 500° C., a pressure between 0.1 and 1 MPa, and an hourly volumetric flow rate of between 0.1 and 10 h$^{-1}$; and
    the catalyst comprises at least one mesostructured material, said mesostructured material comprises:
        (i) a structured mesopore network and walls;
        (ii) silicon and at least one element X selected from the group consisting of aluminum, boron, gallium, indium, and germanium;
        (iii) Si/X molar ratio between 15 and 100;
        (iv) a specific surface area between 100 and 1,200 m$^2$/g; and
        (v) proto-zeolitic entities and/or zeolitic entities in said walls of the mesostructured material.

2. The process according to claim 1, wherein the feedstock comprises isobutanol and optionally other $C_4$ monoalcohols and further comprises a mass ratio of isobutanol to other $C_4$ monoalcohols of greater than 50%.

3. The process according to claim 1, wherein said mesostructured material comprises a mesostructure that is hexagonal 2D, vermicular or cubic 3D.

4. The process according to claim 1, wherein said mesostructured material consists of a spherical elementary particles comprising a diameter that is less than or equal to 200 nm.

5. The process according to claim 1, wherein said mesostructured material comprises a specific surface area of between 300 and 1,000 m$^2$/g.

6. The process according to claim 1, wherein the walls of said mesostructured material comprise proto-zeolitic entities which are radicals for initiating at least one zeolite, wherein the zeolite is selected from among the following zeolites: ZSM-5, ZSM-48, ZSM-22, ZSM-23, ZBM-30, EU-2, EU-11, silicalite, beta, zeolite A, faujasite, Y, USY, VUSY, SDUSY, mordenite, NU-10, NU-87, NU-88, NU-86, NU-85, IM-5, IM-12, theta-1, ferrierite and EU-1.

7. The process according to claim 1, wherein the mesostructured material comprises zeolite nanocrystals trapped in the walls and the structured network of mesopores of said mesostructured material.

8. The process according to claim 1, wherein the walls of said mesostructured material comprise zeolitic entities which are selected from among the following zeolites: ZSM-5, ZSM-48, ZSM-22, ZSM-23, ZBM-30, EU-2, EU-11, silicalite, beta, zeolite A, faujasite, Y, USY, VUSY, SDUSY, mordenite, NU-10, NU-87, NU-88, NU-86, NU-85, IM-5, IM-12, theta-1, ferrierite and EU-1.

9. The process according to claim 1, wherein the catalyst consists integrally of silicon-based mesostructured material.

* * * * *